(12) United States Patent
Miyatani et al.

(10) Patent No.: US 9,983,100 B2
(45) Date of Patent: May 29, 2018

(54) THIN SECTION PREPARATION DEVICE (71) Applicant: SAKURA FINETEK JAPAN CO., LTD., Tokyo (JP)

(72) Inventors: Tatsuya Miyatani, Tokyo (JP); Seigo Murakami, Tokyo (JP)

(73) Assignee: SAKURA FINETEK JAPAN CO., LTD., Tokyo (JP)

( * ) Notice: Subject to any disclaimer, the term of this patent is extended or adjusted under 35 U.S.C. 154(b) by 80 days.

(21) Appl. No.: 14/439,903

(22) PCT Filed: Oct. 25, 2013

(86) PCT No.: PCT/JP2013/078954
§ 371 (c)(1),
(2) Date: Apr. 30, 2015

(87) PCT Pub. No.: WO2014/073394
PCT Pub. Date: May 15, 2014

(65) Prior Publication Data
US 2015/0300924 A1   Oct. 22, 2015

(30) Foreign Application Priority Data

Nov. 8, 2012  (JP) ................................. 2012-246336

(51) Int. Cl.
*G01N 1/06* (2006.01)
*G01N 1/28* (2006.01)
*G01N 1/36* (2006.01)

(52) U.S. Cl.
CPC ............. *G01N 1/06* (2013.01); *G01N 1/2813* (2013.01); *G01N 1/36* (2013.01)

(58) Field of Classification Search
CPC . G01N 1/06; G01N 2035/0439; Y10T 83/222
(Continued)

(56) References Cited

U.S. PATENT DOCUMENTS

| 2,047,262 A | * | 7/1936 | Gibson | ..................... | A21B 5/08 |
| | | | | | 198/445 |
| 2,154,371 A | * | 4/1939 | Alderfer | ................ | B26D 1/225 |
| | | | | | 83/107 |

(Continued)

FOREIGN PATENT DOCUMENTS

| CA | 2661866 A1 | * | 3/2008 | ............... G01N 1/06 |
| CN | 1991330 | | 7/2007 | |

(Continued)

OTHER PUBLICATIONS

Search Report from related EPO Application No. 13853925.9 dated Jun. 17, 2016.

(Continued)

*Primary Examiner* — Jennifer Swinney (57) ABSTRACT

A thin section preparation device includes: a cutting blade (21) which cuts out a thin section (M) from an embedding block (B); a storage tank (7) in which the thin section (M) is floated on a liquid (W) and is spread; a thin-section-conveying-mechanism (8) which conveys the thin section (M) in a direction intersecting in an X axis direction in a state where a first side of the thin section (M) is parallel with the X axis direction; a slide-glass-handling-mechanism (9) which places the thin section (M) floating in the storage tank (7) on a slide glass (G) in a state where a first side of the slide glass (G) is parallel with the X axis direction; and a rotary body (61) which is rotated in a state where the thin section (M) is placed on an outer surface and conveys the thin section (M) toward the slide-glass-handling-mechanism (9).

3 Claims, 5 Drawing Sheets

(58) Field of Classification Search
USPC .......................................................... 83/915.5
See application file for complete search history.

(56) References Cited

U.S. PATENT DOCUMENTS

| | | | | |
|---|---|---|---|---|
| 2,908,936 | A * | 10/1959 | Kilborn .................. | B29C 37/02 |
| | | | | 164/262 |
| 4,932,513 | A * | 6/1990 | Michimae .......... | B65G 47/1471 |
| | | | | 198/397.06 |
| 6,837,362 | B2 * | 1/2005 | van Wijngaarden .. | B65G 51/01 |
| | | | | 198/443 |
| 7,866,464 | B2 * | 1/2011 | Miyatani .................. | G01N 1/06 |
| | | | | 198/844.1 |
| 2007/0199418 | A1 * | 8/2007 | Ito .......................... | B26D 5/007 |
| | | | | 83/13 |
| 2007/0204740 | A1 * | 9/2007 | Miyatani .................. | G01N 1/06 |
| | | | | 83/919 |
| 2008/0044260 | A1 | 2/2008 | Miyatani et al. | |
| 2009/0133556 | A1 * | 5/2009 | Ito ........................... | G01N 1/06 |
| | | | | 83/155 |

FOREIGN PATENT DOCUMENTS

| | | |
|---|---|---|
| JP | 2008-51797 | 3/2008 |
| JP | 2009-109326 | 5/2009 |
| JP | 2009-180546 | 8/2009 |
| JP | 2010-054444 | 3/2010 |
| JP | 2010-261794 | 11/2010 |
| JP | 2010-266394 | 11/2010 |
| WO | 2014/073394 | 5/2014 |

OTHER PUBLICATIONS

Office Action from related Chinese Application No. 201380056085.9 dated Mar. 8, 2016. Partial English translation attached.
International Search Report from corresponding PCT Application No. PCT/JP2013/078954 dated Nov. 26, 2013. English translation attached.
Notice of Allowance from corresponding Japanese Appln. No. 2012-246336 dated Sep. 6, 2016. English translation attached.

* cited by examiner

THIN SECTION PREPARATION DEVICE

TECHNICAL FIELD

The present invention relates to a thin section preparation device.

Priority is claimed on Japanese Patent Application No. 2012-246336, filed Nov. 8, 2012, the content of which is incorporated herein by reference.

BACKGROUND ART

As one of the methods for inspecting and observing a biological sample extracted from a human body, experimental animal, or the like, a method is known in which a thin section is prepared from an embedding block in which the biological sample is embedded by an embedding agent, dye processing is performed on the thin section, and thus, the biological sample is observed.

In the related art, an operation of preparing the thin section is performed manually by an experienced operator using a sharp and thin cutting blade. However, in recent years, an automatic thin-cutting device capable of automatically performing the operation of preparing the thin section has begun to be in use. According to this automatic thin-cutting device, it is possible to continuously prepare the thin section without imposing a burden on the operator.

In the above-described automatic thin-cutting device, the cutting blade and the embedding block are moved relative to each other in a predetermined feeding direction, the embedding block is cut at a thickness of several micrometers (for example, 3 μm to 5 μm), and thus, the thin section can be obtained.

Here, since the thin section obtained by the cutting is cut at an extremely thin thickness, wrinkling or curling easily occurs on the thin section. Accordingly, the thin section obtained by the cutting is floated on a water surface to remove the wrinkling or the curling (spreading process).

Thereafter, the thin section floating on the water surface is scooped by a substrate such as a slide glass, and is placed on the substrate. Accordingly, a thin section sample can be prepared.

In the above-described process of cutting the thin section, in order to decrease a load applied to the biological sample due to the thin-cutting, generally, a method in which the embedding block is cut by the cutting blade having a draw angle is known. In addition, the draw angle is an angle in which an axis line orthogonal to the feeding directions of the cutting blade and the embedding block and an extension direction of the edge of the cutting blade cross each other at an acute angle on a cutting surface formed by the cutting blade.

In addition, in the above-described spreading process, when the thin section is scooped by the substrate and is placed on the substrate, the direction of the thin section with respect to the substrate is varied on the water surface. Accordingly, a portion of the thin section scooped by the substrate protrudes from the substrate, and may not be placed on the substrate.

Therefore, for example, Patent Document 1 discloses a configuration which includes a relay body having a fixing surface to which a thin section is detachably fixed, a holding portion holding the relay body, and moving and rotating means having a rotating table which rotates the relay body around a rotary shaft orthogonal to the fixing surface.

In this configuration, after the thin section floating on the water surface is scooped up on the fixing surface of the relay body in a state where the relay body is held by the holding portion, the relay body is set on the rotating table. In addition, after the relay body is rotated around the rotary shaft, the rotary body is delivered to the substrate. Accordingly, since a relative direction of the thin section with respect to the substrate can be set, it is possible to place the thin section in a predetermined direction on the substrate.

PRIOR ART DOCUMENTS

Patent Documents

Patent Document 1: Japanese Unexamined Patent Application, First Publication No. 2010-261794

SUMMARY OF INVENTION

Problems to be Solved by the Invention

However, in the above-described configuration of Patent Document 1, the moving and rotating means includes a plurality of driving mechanisms (driving shaft) such as the above-described holding portion or rotating table. Accordingly, the mechanism or control of the moving and rotating means becomes complicated. Therefore, the device cost increases, and there is a problem that failure may easily occur.

Accordingly, the aspects of the present invention is made in consideration of the above-described circumstances, and an object thereof is to provide a thin section preparation device capable of simplifying the configuration, decreasing the cost, and preparing a thin section sample having high reliability.

Means for Solving the Problems

A thin section preparation device which is an aspect of the present invention adopts the following configurations.

(1) A thin section preparation device that is capable to cut a thin section from an embedding block in which a biological sample is embedded, and to prepare a thin section sample by placing the thin section on a substrate, the thin section preparation device comprising: a cutting blade that is configured to relatively move with respect to the embedding block in an X axis direction in which a first side of the embedding block extends, and to thinly cut the embedding block with a predetermined draw angle in order to cut out the thin section; a storage tank that is configured to store a liquid, and to spread the thin section by floating the cut thin section on the liquid; a conveying mechanism that is arranged so that a first portion of the conveying mechanism is disposed in a state where the first portion is close to a blade edge of the cutting blade while having a second portion of the conveying mechanism immersed into the liquid, and that is configured to convey the thin section in a direction intersecting in the X axis direction in a plan view of a surface of the embedding block in a state where the first side of the thin section is parallel with the X axis direction; a substrate disposition mechanism that is configured to place the thin section floating in the storage tank on the substrate in a state where a first side of the substrate is parallel with the X axis direction in the plan view; and a rotary body that is provided between the conveying mechanism and the substrate disposition mechanism, and that is configured to convey the thin section toward the substrate disposition mechanism by rotating in a state where the thin section is placed on an outer surface of the rotary body, wherein the rotary body is configured to be rotatable about a Y axis orthogonal to the X axis direction in the plan view in a state where a portion of the rotary body is immersed into the liquid of the storage tank.

According to this configuration, the thin section is conveyed in the state where the thin section thinly cut with the draw angle is conveyed by the conveying mechanism without changing the direction of the thin section in the state where the first side of the thin section is coincident in the X axis direction, and the thin section is spread. Thereafter, in the thin section, the conveyance direction is changed to the X axis direction by the rotary body in the state where the first side of the thin section is coincident in the X axis direction. Accordingly, the first side of the thin section is conveyed to the substrate disposition mechanism in the state where the first side of the thin section is coincident with the first side of the substrate. As a result, it is possible to place the thin section in a desired direction with respect to the substrate at a desired position on the substrate. Accordingly, wrinkling, curling, or the like of the thin section which occurs when the thin section is placed on the substrate is prevented, and thus, it is possible to prepare the thin section sample having high reliability.

In addition, unlike the related art, since it is not necessary to provide the plurality of driving shafts, it is possible to simplify the configuration and decrease the cost.

(2) According to the thin section preparation device of above mentioned (1), the rotary body may include a plurality of support portions which support the thin section with an interval in a plane direction of the thin section.

According to this configuration, the thin section is supported by the plurality of support portions with an interval in the plane direction of the thin section. Accordingly, when the thin section is floated on the liquid surface between the conveying mechanism and the rotary body, it is possible to remove bubbles mixed between the liquid surface and the thin section through the above-described intervals of the rotary body. Therefore, when the thin section is placed on the substrate, it is possible to prevent the bubbles from being mixed between the substrate and the thin section, and thus, it is possible to improve adhesion between the substrate and the thin section. Accordingly, since it is possible to prepare the thin section sample having higher reliability, it is possible to smoothly perform a post-process (for example, dyeing process).

(3) According to the thin section preparation device of above mentioned (1) or (2), the thin section preparation device may further include a slider mechanism that is configured to move the conveying mechanism and the rotary body relative to each other in a direction of the blade edge of the cutting blade.

According to this configuration, by a Y axis direction component of a movement speed vector in the direction of the blade edge of the cutting blade by the slider mechanism, the Y axis direction component in the conveyance speed vector in the conveyance direction by the conveying mechanism is cancelled, and thus, the thin section relatively moves in only the X axis direction with respect to the rotary body.

Therefore, in one thin section, it is possible to decrease a difference between movement speeds in the Y axis direction between a portion which is placed on the rotary body and a portion which is positioned on the conveying mechanism and the liquid surface. Accordingly, wrinkling, rupturing, or the like of the thin section is prevented, and it is possible to smoothly deliver the thin section to the rotary body.

Advantage of Invention

According to the thin section preparation device of the aspects of the present invention, it is possible to simplify the configuration, decrease the cost, and prepare a thin section sample having high reliability.

DESCRIPTION OF EMBODIMENTS

Next, an embodiment of the present invention will be described with reference to the drawings.

<Configuration of Automatic Thin-Cutting Device>

Figure 1:
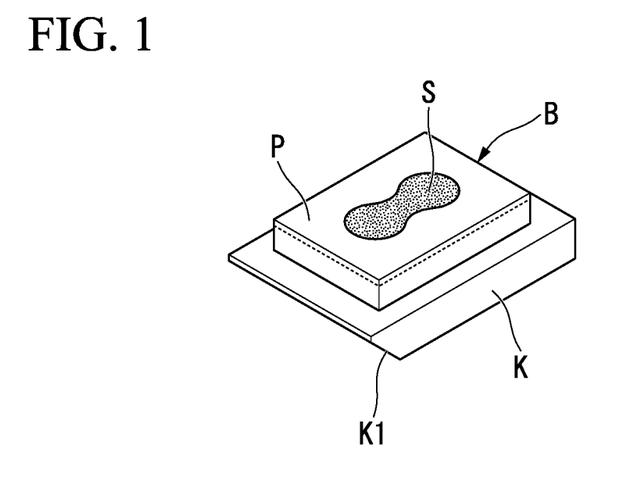
FIG. 1 is a perspective view of an embedding block which is conveyed by an automatic thin-cutting device according to the present invention.
Figure 2:
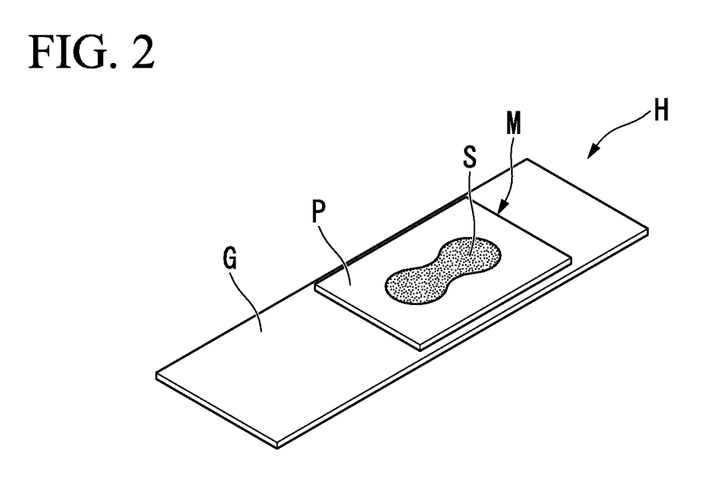
FIG. 2 is a perspective view of a thin section sample which is prepared by the automatic thin-cutting device according to the present invention.

FIG. 1 is a perspective view of an embedding block B which is conveyed by an automatic thin-cutting device 1. FIG. 2 is a perspective view of a thin section sample H which is prepared by the automatic thin-cutting device 1.

As shown in FIG. 1, the automatic thin-cutting device 1 (refer to FIG. 3) of the present embodiment is a device which thinly cuts the embedding block B, in which a biological sample S is embedded by a paraffin P serving as an embedding material, to a thickness of 3 µm to 5 µm, for example. Accordingly, it is possible to prepare a thin section M shown in FIG. 2 by the automatic thin-cutting device 1.

In addition, the automatic thin-cutting device 1 of the present embodiment not only can prepare the thin section M but also can automatically perform an operation of storing the thin section samples H in a basket after transferring the thin section M to the substrate such as a slide glass G and preparing the thin section samples H.

In addition, the embedding block B is a rectangular block in a plan view in which moisture in the formalin-fixed biological sample S is paraffin-substituted, and thereafter, the periphery is hardened in a block shape by the paraffin P. Accordingly, the biological sample S is embedded in the paraffin P. In addition, for example, the biological sample S is a tissue such as an internal organ extracted from a human body, experimental animal, or the like, and is a tissue which is appropriately selected in a medical field, a pharmaceutical field, a food field, a biological field, or the like.

In addition, as shown in FIG. 1, the embedding block B is fixed to a cassette K.

The cassette K is formed in a box shape by a resin having chemical resistance or the like, and has a role as a fixing table which fixes the embedding block B. One side surface of the cassette K is an inclined surface K1 in which the surface faces downward. ID data (not shown), which includes a production number of the cassette K, a preparation date of the embedding block B, various data of the biological sample S, or the like, is recorded on the inclined surface K1. Accordingly, it is possible to manage the quality of the embedding block B by reading the ID data.

Subsequently, each component of the automatic thin-cutting device 1 will be described.

In the present embodiment, first, components configuring the automatic thin-cutting device 1 are sequentially and simply described, and thereafter, the necessary components are described in detail.

Figure 3:
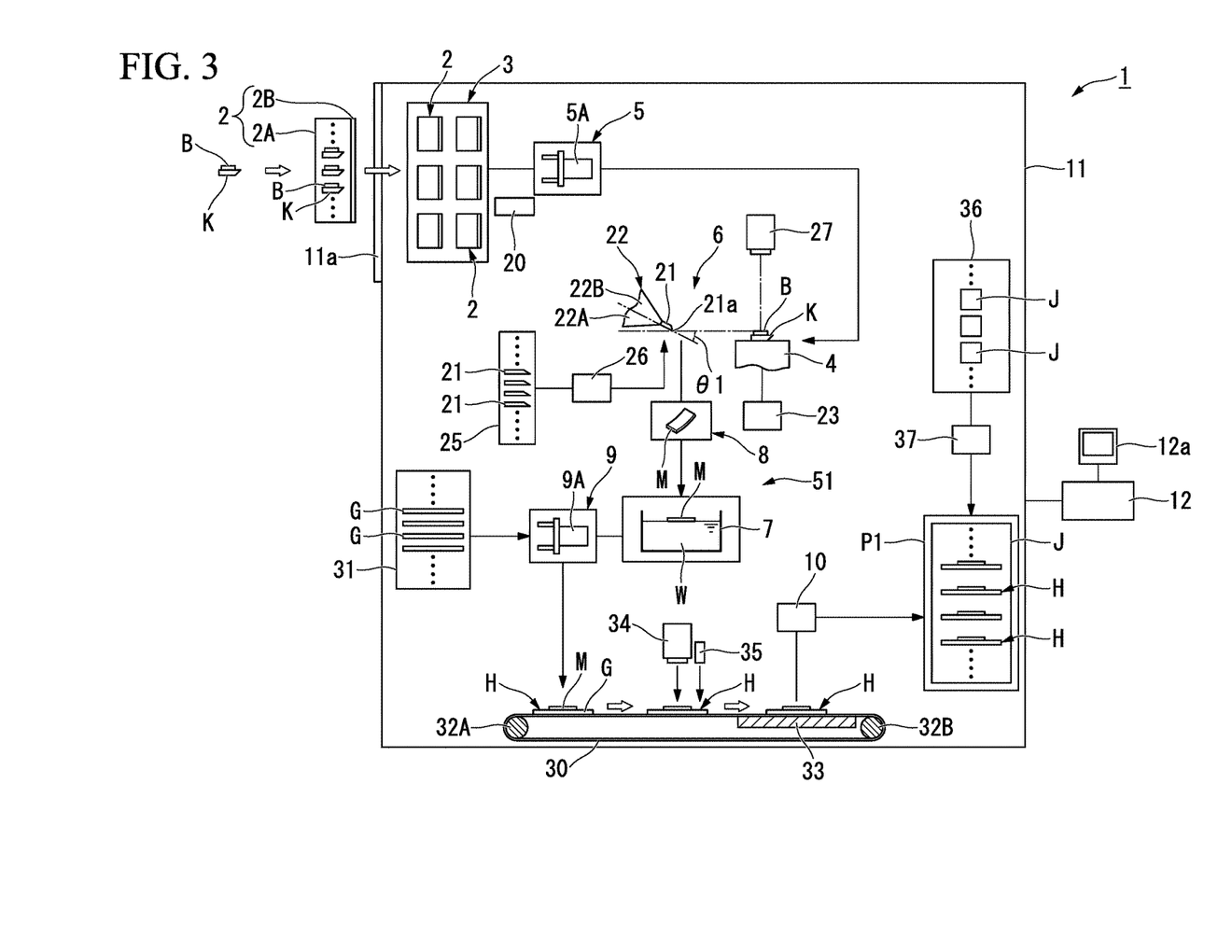
FIG. 3 is a schematic configuration view of the automatic thin-cutting device.

As shown in FIG. 3, the automatic thin-cutting device 1 mainly includes a plurality of magazines 2, a carousel 3, a block transport mechanism 5, a thin-cutting mechanism 6, a thin section conveying mechanism (conveying mechanism) 8, a slide glass handling mechanism (substrate disposition mechanism) 9, a slide glass storage mechanism 10, a device case 11 which accommodates the components in the inner portion, and a controller 12 which totally controls the components. The plurality of embedding blocks B is stored in the plurality of magazines 2 so as to be inserted or removed. Each magazine 2 is individually detachably mounted on the carousel 3. The block transport mechanism 5 inserts or removes one embedding block B which is selected among the plurality of embedding blocks B stored in the magazine 2 mounted on the carousel 3, and places the embedding block B on a stage 4. The thin-cutting mechanism 6 cuts the embedding block B placed on the stage 4 at a predetermined thickness, and the cutting of thin section M is performed. The thin section conveying mechanism (conveying mechanism) 8 conveys the thin section M cut by the thin-cutting mechanism 6 to the storage tank 7, and floats the thin section M on a liquid surface to spread the thin section M. The slide glass handling mechanism (substrate disposition mechanism) 9 scoops the spread thin section M from the liquid surface onto the slide glass G, and prepares the thin section sample H. The slide glass storage mechanism 10 stores the prepared thin section sample H in a basket J.

(Device Case)

The inner portion of the above-described device case 11 can be sealed, and for example, in the inner portion, an environmental condition such as humidity, temperature, or the like can be set to a desired condition. An access door 11*a* which is opened and closed by an operator is provided on the wall surface of the device case 11. The access door 11*a* is a door which is used when the magazine 2 is mounted or extracted. By opening the access door 11*a*, access to the carousel 3 on which the magazine 2 is mounted is possible.

(Magazine)

The magazine 2 is a storage case in which the entirety is formed in a vertically long rectangular parallelepiped shape. The magazine 2 can store the plurality of embedding blocks B fixed to the cassettes K in a state where the embedding blocks B are arranged in a height direction. The magazine 2 mainly includes a box-shaped magazine main body 2A in which the front surface is opened, and an opening and closing door 2B which is fixed to the magazine main body 2A.

When the opening and closing door 2B is in a closed state, a portion of the plurality of embedding blocks B stored in the magazine main body 2A is covered, and thus, dropping of the embedding block B is prevented. Accordingly, the operator can carry the magazine 2 at ease without paying attention to the dropping of the embedding block B.

(Carousel)

The magazine 2 configured as described above is detachably mounted on the carousel 3. In the illustrated example, six magazines 2 are simultaneously mounted on the carousel 3.

The carousel 3 is disposed at a position at which access is possible from the outside by opening an access door 11*a* of the device case 11. Accordingly, the magazine 2 can be mounted on the carousel 3 or removed from the carousel 3 manually by the operator.

In addition, the carousel 3 can rotate about a vertical axis. The carousel 3 moves the magazine 2 mounted by the rotation in a circumferential direction, and can set one selected magazine 2 to a block extraction position at which the magazine 2 faces the block transport mechanism 5. Moreover, the operation of the carousel 3 is controlled by the controller 12.

In addition, in FIG. 3, the illustration of the carousel 3 is simplified.

(Reading Portion)

A reading portion 20 is disposed at a position adjacent to the carousel 3. The reading portion 20 reads ID data printed on the cassette K of each embedding block B which is stored in the magazine 2 positioned at the above-described block extraction position.

For example, the reading portion 20 and the magazine 2 positioned at the block extraction position are configured to move relative to each other in a vertical direction. According to this relative movement, the reading portion 20 can read the ID data printed on the cassette K of all embedding blocks B stored in the magazine 2. In addition, the reading portion 20 optically reads the ID data and outputs the read ID data to the controller 12.

(Block Transport Mechanism)

The block transport mechanism 5 is a handling robot which includes a hand portion 5A capable of holding the cassette K which fixes the embedding block B. The block transport mechanism 5 is positioned at the position adjacent to the carousel 3. Based on the instruction from the controller 12, the block transport mechanism 5 holds one embedding block B, which is stored in the magazine 2 positioned at the block extraction position among the magazines 2 mounted on the carousel 3, by the hand portion 5A, can insert and remove the held embedding block B from the magazine 2, or can place the embedding block on the stage 4.

(Stage)

In the stage 4, an actuator is incorporated into the inner portion, and the stage 4 is configured to appropriately move vertically based on the instructions from the controller 12. Accordingly, it is possible to adjust the height of the embedding block B placed on the stage 4, and it is possible to thinly cut the embedding block B at a desired thickness (for example, 5 μm).

In addition, the stage 4 is a multi-axial stage in which rotation about the vertical axis and swing about a horizontal axis (two axes) can be performed. Therefore, the stage 4 freely controls the posture of the embedding block B, and can set the orientation, the inclination, or the like of the embedding block B to a desired state.

(Thin-Cutting Mechanism)

The thin-cutting mechanism 6 includes a cutting blade 21 which is disposed in the vicinity of the stage 4, a holder 22 which holds the cutting blade 21 in an exchangeable manner, and a moving mechanism 23. The moving mechanism 23 moves the stage 4 with respect to the cutting blade 21, and thinly cuts the embedding block B by the cutting blade 21.

The cutting blade 21 is a long blade in which one end side becomes a blade edge 21*a*. The cutting blade 21 is obliquely held (clamp-fixed) to the holder 22 with a predetermined rake angle θ1. In addition, in the illustrated example, the blade edge 21*a* is a single edge. However, the blade edge may be a double edge.

The holder 22 mainly includes a placing plate 22A and a pressing plate 22B. The cutting blade 21 is placed on the placing plate 22A in a state where the blade edge 21a is exposed to the outside. The pressing plate 22B presses the placed cutting blade 21 to the placing plate 22A, and the cutting blade 21 is clamp-fixed.

The moving mechanism 23 includes a guide rail (not shown) and a driving portion (not shown) which reciprocates the stage 4 along the guide rail at a predetermined speed, thinly cuts the embedding block B by the cutting blade 21 clamp-fixed by the holder 22 by reciprocating the stage 4 based on the instruction from the controller 12, and performs the cutting of the thin section M.

In addition, the stage 4 raises the embedding block B by a predetermined amount according to the reciprocation by the moving mechanism 23. Accordingly, the embedding block B is cut at a predetermined thickness, and it is possible to prepare the thin section M.

In addition, in the present embodiment, the moving mechanism 23 is configured so that the stage 4 side moves with respect to the cutting blade 21. However, the moving mechanism 23 may be configured so that the cutting blade 21 side moves with respect to the stage 4, or may be configured so that the holder 22 side and the stage 4 side move together.

In either case, the moving mechanism 23 may be designed in any manner as long as the embedding block B and the cutting blade 21 move relative to each other and the thin-cutting can be performed by the cutting blade 21.

(Storage Case and Cutting Blade Transport Mechanism)

A plurality of the cutting blades 21 are stored in the storage case 25 in a state of being multiply stacked. After the cutting blades 21 are extracted one by one as necessary by the cutting blade transport mechanism 26, the cutting blade 21 is transported to the holder 22 and clamp-fixed. That is, the cutting blade 21 can be replaced at a predetermined timing.

Based on the instructions from the controller 12, the cutting blade transport mechanism 26 inserts a new cutting blade 21 extracted from the storage case 25 into a portion between the placing plate 22A and the pressing plate 22B in the holder 22, and pushes out and transports the used cutting blade 21 from the holder 22. Accordingly, the replacement of the cutting blade 21 is performed. After a new cutting blade 21 is set, the pressing plate 22B of the holder 22 is operated to perform the clamp-fixing of the new cutting blade 21 according to the instruction of the controller 12.

In addition, the used cutting blade 21 pushed out from the holder 22 is sent to a waste bottle (not shown) or the like via a waste chute (not shown) or the like.

(First Imaging Camera)

A first imaging camera 27 which images the embedding block B placed on the stage 4 is disposed above the stage 4. The first imaging camera 27 images the embedding block B which is illuminated by illumination light from a light source (not shown). In this case, the first imaging camera 27 can image the surface state or the internal state of the embedding block B according to the type (for example, vertical illumination light or diffused illumination light) of the illumination light.

In addition, the captured image is sent to the controller 12, is recorded, and for example, is displayed on a monitor 12a connected to the controller 12.

(Thin Section Conveying Mechanism)

Based on the instruction from the controller 12, the thin section conveying mechanism 8 is a mechanism which transports the thin section M cut by the thin-cutting mechanism 6 up to the storage tank 7 and floats the thin section M on the liquid surface. For example, the thin section conveying mechanism 8 may use a conveyance belt, a transport tape, or the like.

(Storage Tank)

A liquid W such as water which is adjusted to a predetermined temperature is stored in the storage tank 7. In the storage tank 7, the thin section M floating on the liquid surface is spread using a surface tension. In addition, the stored liquid W is discharged from the storage tank 7 via a circulation pipeline (not shown) as necessary, and is supplied into the storage tank 7. Accordingly, a clear liquid W is stored in the storage tank 7 at all times.

(Slide Glass Handling Mechanism)

The slide glass handling mechanism 9 is a handling robot which includes the hand portion 9A capable of holding the slide glass G, and is disposed at a position adjacent to the storage tank 7. The slide glass handling mechanism 9 is operated based on the instruction from the controller 12 and scoops the spread thin section M floating on the liquid on the slide glass G held by the hand portion 9A to transfer the thin section M, and thus, it is possible to prepare the thin section sample H.

After the slide glass handling mechanism 9 scoops the thin section M on the slide glass G and prepares the thin section sample H, the slide glass handling mechanism 9 delivers the thin section sample H onto a sample conveyance belt 30. Thereafter, the slide glass handling mechanism 9 holds a new slide glass G among the slide glasses G stored in a slide glass storage portion 31 and moves the new slide glass G to a standby state for scooping the next thin section M.

The slide glass storage portion 31 is disposed in the vicinity of the storage tank 7, and for example, several dozens to several hundreds of unused slide glasses G are stored in the inner portion of the slide glass storage portion 31.

(Sample Conveyance Belt and Hot Plate)

For example, the above-described sample conveyance belt 30 is a conveyance belt which is wound between a driving pulley 32A and a driven pulley 32B which are driven based on the instruction from the controller 12. The sample conveyance belt 30 can transport the thin section sample H to the downstream side by driving of the driving pulley 32A.

The hot plate 33 which is heated to a predetermined temperature is disposed at the downstream side in the conveyance direction of the sample conveyance belt 30. The hot plate 33 heats the thin section sample H placed on the sample conveyance belt 30 in a state where the thin section sample H is interposed between the hot plate 33 and the sample conveyance belt 30. Accordingly, superfluous liquid W remaining on the thin section sample H can be removed by vaporization, and it is possible to further spread the thin section M while preventing the existence of the liquid W between the slide glass G and the thin section M.

(Second Imaging Camera and Recording Portion)

In the present embodiment, while the thin section sample H is conveyed up to the downstream side at which the hot plate 33 is disposed by the sample conveyance belt 30, the imaging of the thin-cutting state in the thin section M using a second imaging camera 34 and the printing of individual data to the slide glass G using a recording portion 35 are performed.

The second imaging camera 34 is disposed above the sample conveyance belt 30, images the thin section M until the thin section sample H placed on the sample conveyance belt 30 is conveyed to the downstream side, and sends the captured image to the controller 12. The captured image of the second imaging camera 34 sent to the controller 12 is recorded in the controller 12, and for example, is displayed on the monitor 12a.

For example, the recording portion 35 is a laser marker and is disposed to be adjacent to the second imaging camera 34. Based on the instructions from the controller 12, the recording portion 35 irradiates the slide glass G with laser light and performs the printing of the individual data. In this case, similar to the second imaging camera 34, the recording portion 35 performs the printing until the thin section sample H is conveyed to the downstream side.

(Slide Glass Storage Mechanism)

The slide glass storage mechanism 10 is disposed above the sample conveyance belt 30, and is a mechanism which stores the thin section sample H on the sample conveyance belt 30 heated by the hot plate 33 in the basket J, based on the instruction from the controller 12. For example, as this mechanism, the thin section sample H is pushed out from the sample conveyance belt 30 using a pushing out rod driven by a cylinder or the like and may be stored in the basket J, or the thin section sample H may be stored in the basket J using a robotic hand or the like.

(Basket)

For example, the basket J is a dye basket, and can store several thin section samples H to several dozens of thin section samples H at once. The plurality of baskets J are stored in a basket storage portion 36 in advance. After the baskets J stored in the basket storage portion 36 are sequentially extracted by a basket supply mechanism 37 which is operated based on the instruction from the controller 12, the baskets J are set at a sample storage position P1. At the sample storage position P1, the thin section samples H are stored in the basket J.

When the thin section samples H having the predetermined number of sheets are stored in the basket J, the basket J is sent into a storage cabinet (not shown) so as to be stored. At this time, warm wind adjusted to a predetermined temperature circulates through the storage cabinet, and thus, the thin section samples H are dried at an optimal state.

(Thin Section Preparation Device)

Next, among the above-described components, a thin section preparation device 51 which includes the thin-cutting mechanism 6, the thin section conveying mechanism 8, the storage tank 7, and the slide glass handling mechanism 9 will be described in detail.

Figure 4:
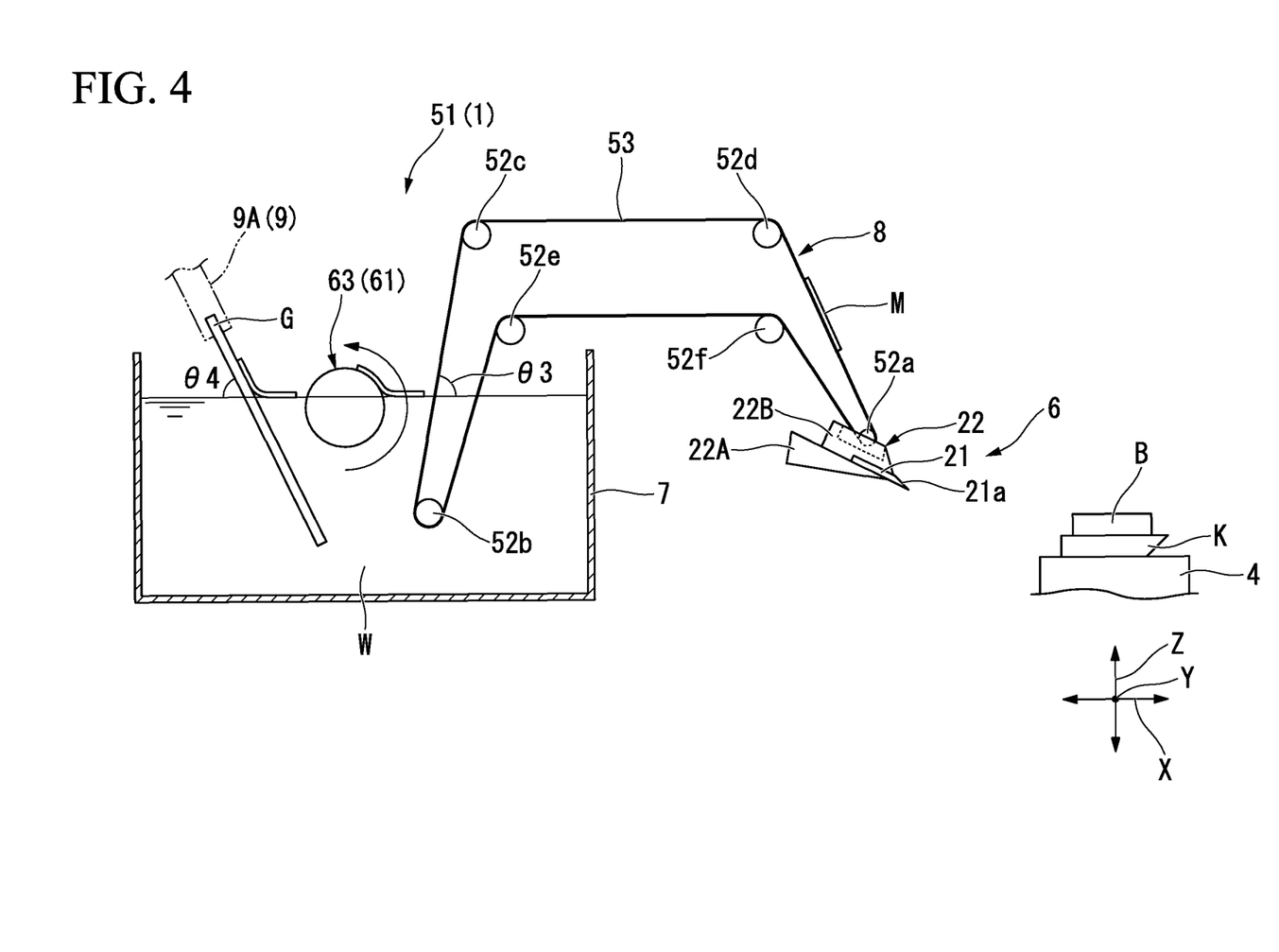
FIG. 4 is a schematic cross-sectional view of a thin section preparation device taken along line A-A of FIG. 5.
Figure 5:
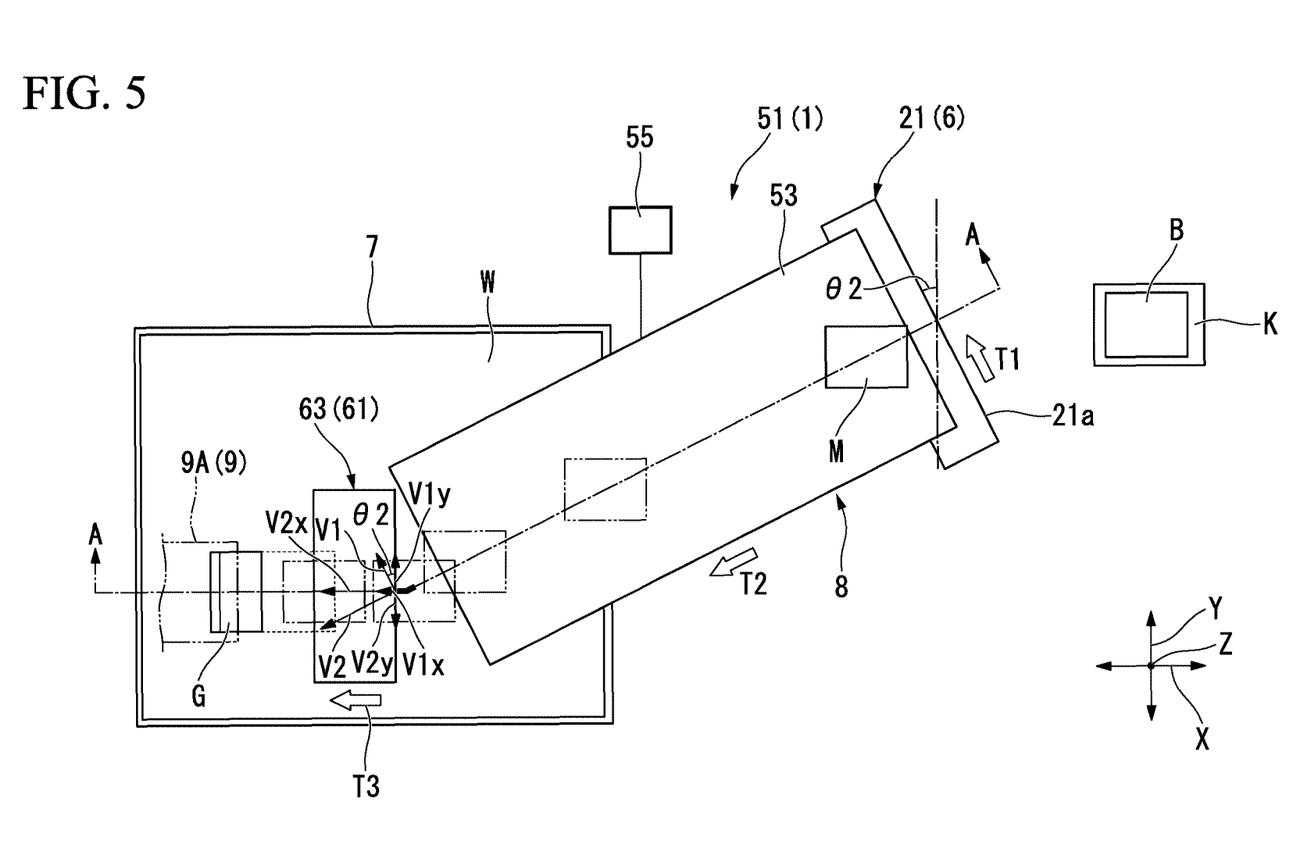
FIG. 5 is a schematic plane view of the thin section preparation device.

FIG. 4 is a schematic side view of the thin section preparation device 51 taken along line A-A of FIG. 5. FIG. 5 is a schematic plan view of the thin section preparation device 51. In addition, in descriptions below, the vertical direction is defined as a Z axis direction, the movement direction described below of the stage 4 on the horizontal surface orthogonal to the Z axis direction is defined as an X axis direction, and a direction orthogonal to the X axis direction is defined as a Y axis direction.

As shown in FIGS. 4 and 5, the moving mechanism 23 of the thin-cutting mechanism 6 is configured to reciprocate along the X axis direction. That is, the moving mechanism 23 of the thin-cutting mechanism 6 is configured to reciprocate to be parallel with the X axis direction. The moving mechanism 23 of the thin-cutting mechanism 6 moves the embedding block B in parallel with a first side (a side along a longitudinal direction, a side parallel with the longitudinal direction) among the surfaces of the embedding block B placed on the stage 4.

The cutting blade 21 is disposed with respect to the embedding block B with a predetermined draw angle θ2.

Specifically, the cutting blade 21 is disposed to be inclined in the Y axis direction orthogonal to the X axis direction, and the blade edge 21a is inclined to the side along the short-length direction (a side parallel to the short-length direction) among the surfaces of the embedding block B placed on the stage 4 and faces the side. Accordingly, during the thin-cutting, the blade edge 21a of the cutting blade 21 enters the embedding block B from the vicinity of the corner portion.

The thin section conveying mechanism 8 includes a plurality of conveyance rollers 52a to 52f, a conveyance belt 53, and the above-described driving portion (not shown) which rotates the conveyance rollers 52a to 52f. The conveyance belt 53 is wound around the conveyance rollers 52a to 52f, and conveys the thin section M in the state where the thin section M is placed on the upper surface of the conveyance belt 53.

The conveyance rollers 52a to 52e are rotatably supported by a frame (not shown) so that the axial direction of the rotary shaft of each transport roller is inclined by the angle equal to the draw angle θ2 (is parallel with a direction T1 of the blade edge which is the extension direction of the blade edge). Specifically, the conveyance rollers 52a to 52f include the first roller 52a which is disposed to be close to the blade edge 21a, the second roller 52b which is disposed in the storage tank 7, and the plurality of intermediate rollers 52c to 52f which are disposed between the first roller 52a and the second roller 52b. In addition, the first roller 52a is supported by the frame with a gap through which the conveyance belt 53 can pass between the first roller 52a and the holder 22 of the cutting blade 21. In addition, the intermediate rollers 52c to 52f are disposed above the first roller 52a and the second roller 52b.

The conveyance belt 53 is an endless belt which is wound to abut the intermediate rollers 52c to 52f between the first roller 52a and the second roller 52b. The vicinity of the second roller 52b in the conveyance belt 53 is immersed into the storage tank 7. In this case, the conveyance belt 53 intersects the liquid surface of the storage tank 7 at a predetermined angle θ3. In addition, a running direction T2 of the conveyance belt 53 of the present embodiment becomes a direction orthogonal to the direction T1 of the blade edge of the cutting blade 21 in a plan view of the XY plane.

For example, the driving portion is connected to any of the intermediate rollers 52c to 52f. The driving portion is driven, the conveyance belt 53 runs in an endless manner in the running direction T2, and thus, the thin section M can convey from one portion (first portion) on the conveyance belt 53 toward the other portion (second portion). In addition, the operation of the driving portion is controlled by the controller 12.

The thin section conveying mechanism 8 includes a slider mechanism 55 which reciprocates the frame (conveyance belt 53 and the conveyance rollers 52a to 52f) along the direction (the direction T1 of the blade edge) orthogonal to the running direction T2 on the XY plane. Moreover, for example, the slider mechanism 55 includes a driving portion such as a guide rail which supports the frame and a servo motor which moves the frame along the guide rail.

For example, the liquid W such as water, hot water, or a specific solution is stored in the storage tank 7. In addition, the storage tank 7 is designed to a sufficient length in the direction T1 of the blade edge so that the storage tank 7 does not interfere with the frame when the frame moves in parallel with the direction T1 of the blade edge by the slider mechanism 55.

In the slide glass handling mechanism 9, the above-described hand portion 9A can be moved between the storage tank 7 and the slide glass storage portion 31 by the operation of the driving portion (not shown). Specifically, in the state where the hand portion 9A holds one end portion in the longitudinal direction of the slide glass G, the hand portion 9A can move between an immersion position at which the slide glass G is immersed into the storage tank 7 and a replacement position at which the slide glass G is replaced at the slide glass storage portion 31. In this case, in the above-described immersion position, the slide glass G is immersed in the state where the first side is coincident with the X axis direction in the longitudinal direction in a plan view and the other end portion in the longitudinal direction is inclined at a predetermined angle θ4 with respect to the liquid surface.

Figure 6:
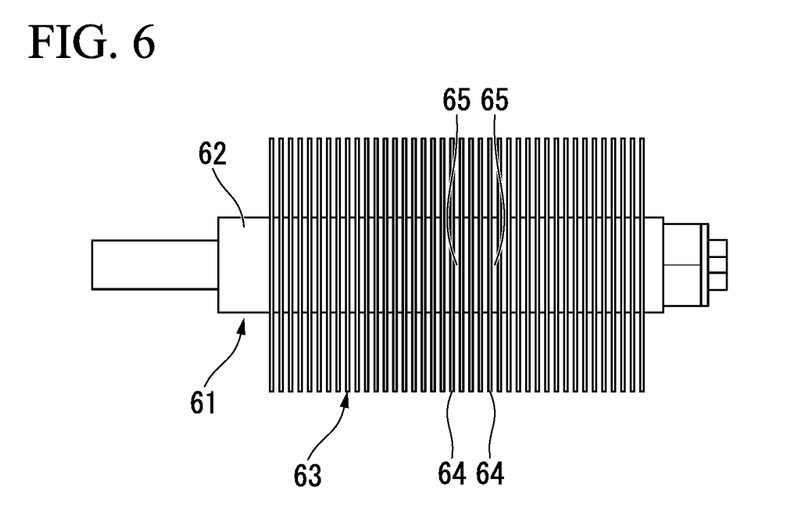
FIG. 6 is a plan view of a rotary body.

FIG. 6 is a plan view of the rotary body 61.

Here, as shown in FIGS. 4 to 6, in the above-described storage tank 7, the rotary body 61 is immersed between the second portion of the conveyance belt 53 of the thin section conveying mechanism 8 and the immersion position of the slide glass G by the slide glass handling mechanism 9. The rotary body 61 includes a rotary shaft 62 which is rotatably supported about the Y axis by the driving portion (not shown), and a thin section support body 63 which is attached to the rotary shaft 62.

In the thin section support body 63, a plurality of ring members (support portions) 64 are laminated via spacers 65. The thin section support body 63 is attached to the rotary shaft 62 in a state where the center axis of each of the ring members 64 is coincident with the axial direction of the rotary shaft 62. Accordingly, the entirety of the thin section support body 63 is formed in columnar shape, and the thin section support body 63 is immersed into the liquid W in a state where a portion thereof (the upper portion) is exposed to the liquid surface. In addition, the diameter of the above-described spacer 65 is smaller that of the ring member 64, and a gap is formed between outer circumferential portions of the ring members 64 adjacent in the Y axis direction.

In addition, the thin section support body 63 is rotated about the Y axis according to the rotation of the rotary shaft 62 in the state where the thin section M is supported by the outer circumferential surfaces of the ring members 64, and thus, the thin section M is conveyed along the X axis direction (refer to the conveyance direction T3).

Moreover, on the liquid surface of the storage tank 7, a distance in the X axis direction between the outer circumferential surface of the thin section support body 63 and the upper surface of the conveyance belt 53, and a distance in the X axis direction between the outer circumferential surface of the thin section support body 63 and the slide glass G disposed at the immersion position are set to be equal to or less than the length in the longitudinal direction of each of the thin sections M, or to be less than the length in the longitudinal direction of each of the thin sections M.

For example, the controller 12 controls a movement speed in the direction T1 of the blade edge of the cutting blade 21 by the above-described slider mechanism 55, and a conveyance speed (running speed) in the running direction T2 by the conveyance belt 53 under the following conditions.

That is, the controller 12 controls the speeds so that a Y axis direction component V1y of a movement speed vector V1 in the direction T1 of the blade edge of the cutting blade 21 by the slider mechanism 55 and a Y axis direction component V2y of a conveyance speed vector V2 in the running direction T2 by the conveyance belt 53 equally act on each other in the direction opposite to each other, and an X axis direction component V1x of the movement speed vector V1 and an X axis direction component V2x of the conveyance speed vector V2 act on each other in the same direction. Specifically, the controller 12 controls the speeds so that at least V1 cos θ2−V2 sin θ2=0 is satisfied.

In addition, the controller 12 controls a rotating speed of the rotary body 61 so that the rotating speed is equal to or less than the conveyance speed (running speed) of the conveyance belt 53.

<Operation of Automatic Thin-Cutting Device>

Next, the operation of the automatic thin-cutting device 1 configured as described above will be described.

Moreover, in the present embodiment, first, the overall flow until the thin section sample H is prepared is simply described, and thereafter, the flow of the partial process will be described in detail.

First, as advance preparation, the operator stores cassettes K, to which embedding blocks B are fixed, in the plurality of magazines 2. Thereafter, the operator opens the access door 11a of the device case 11, and mounts the magazines 2 on the carousel 3. After each magazine 2 is mounted on the carousel 3, the access door 11a is closed. In addition, the operator confirms whether or not the cutting blade 21 is appropriately set into the storage case 25, whether or not the slide glass G is appropriately set to the slide glass storage portion 31, whether or not the basket J is appropriately set to the basket storage portion 36, or the like, and thus, the advance preparation ends.

After the advance preparation ends, the operator starts the operation of each component in the device case 11 through the controller 12.

As described above, when the operation of each component in the device case 11 starts, the controller 12 sequentially rotates the carousels 3 and reads the ID data by the reading portion 20, and thereafter, the embedding block B is held by the block transport mechanism 5 using the hand portion 5A. Subsequently, after the held embedding block B is extracted from the magazine 2 by the block transport mechanism 5, the embedding block B is placed on the stage 4 via the cassette K.

When the setting operation of the embedding block B on the stage 4 ends, the controller 12 starts the thin-cutting operation of the embedding block B.

First, the upper surface of the embedding block B is adjusted to a desired height position by adjusting the height of the stage 4. In addition, the moving mechanism 23 of the thin-cutting mechanism 6 reciprocates the stage 4, and thus, the embedding block B is thinly cut by the cutting blade 21 which is clamped-fixed by the holder 22. Accordingly, it is possible to perform rough-flattening of the embedding block B.

When the thin-cutting is performed, the first imaging camera 27 images the embedding block B. This captured image is recorded in the controller 12 and is displayed on the monitor 12a. Accordingly, the operator can confirm the surface state or the internal state of the embedding block B by the captured image which is displayed on the monitor 12a. Moreover, with reference to the captured image, it is possible to incline or rotate an appropriate stage 4 during the thin-cutting. As a result, it is possible to expose an optimal surface to the surface by rough machining of the embedding block B.

In addition, when a flattening operation is performed by the above-described rough machining, the operation in which the thin section M is conveyed to the storage tank 7 by the thin section conveying mechanism 8 is not performed.

Accordingly, the thin section M generated during this process becomes cutting chips and is collected to a collection portion (not shown).

Subsequently, after the flattening of the embedding block B ends, the controller 12 transfers the operation of the automatic thin-cutting device 1 from the rough machining operation to a main machining operation. At this time, the controller 12 operates the cutting blade transport mechanism 26, and replaces the cutting blade 21 used in the rough machining with a new cutting blade 21. Moreover, the replacement of the cutting blade 21 is not limited to this case, and may be appropriately performed if necessary. Moreover, in the present embodiment, the predetermined draw angle θ2 is applied to the cutting blade 21, and thus, it is possible to decrease the load to the biological sample S due to the thin-cutting.

When the operation is transferred to the main machining operation, the controller 12 prepares the thin section M by the thin-cutting mechanism 6, conveys the prepared thin section M to the storage tank 7 by the thin section conveying mechanism 8, and floats the thin section on the liquid surface. Accordingly, the thin section M is spread, and curling or the like generated during the thin-cutting is removed.

Subsequently, the controller 12 operates the slide glass handling mechanism 9, scoops the thin section M floating on the liquid surface onto the slide glass G, and prepares the thin section sample H. The slide glass handling mechanism 9 places the prepared thin section sample H on the sample conveyance belt 30 and delivers the thin section sample H.

Moreover, the controller 12 drives the driving pulley 32A, and conveys the thin section sample H placed on the sample conveyance belt 30 toward the downstream side. Then, while the thin section sample H is conveyed to the hot plate 33, the second imaging camera 34 images the thin section M, and the captured image is sent to the controller 12.

Based on the captured image sent from the second imaging camera 34, the controller 12 determines whether or not the thin section M subjected to the main machining is appropriately cut thinly. Here, when the controller 12 determines that the thin-cutting is good, the controller 12 operates the recording portion 35, the individual data associated with the ID data read from the cassette K is recorded in the slide glass G of the thin section sample H.

In addition, the thin section sample H in which the individual data is recorded is further conveyed to the downstream side of the sample conveyance belt 30 and is heated by the hot plate 33. Moreover, the controller 12 operates the slide glass storage mechanism 10 and stores the heated thin section sample H in the basket J.

As the determination result with respect to the quality of thin-cutting, when the controller 12 determines that the thin-cutting is not good, the controller 12 does not operate the slide glass storage mechanism 10, and delivers the thin section sample H from the sample conveyance belt 30 to a defective product discharging chute (not shown). Accordingly, the thin section sample H which is the defective product is not stored in the basket J and is collected.

When the thin section samples H which are determined as good products are stored in the basket J by a predetermined number, the basket J is sent to the storage cabinet and is stored, the basket supply mechanism 37 extracts a new basket J from the basket storage portion 36 and sets the new basket J at the sample storage position P1, and subsequent storage operations are prepared.

As described above, according to the automatic thin-cutting device 1 of the present embodiment, not only the thin section M is automatically prepared but also the thin section sample H is automatically prepared, and it is possible to store the thin section samples H in the basket J by a predetermined number.

Accordingly, the operator can transfer the basket J to the dyeing process of the biological sample S directly by extracting the appropriate basket J from the storage cabinet, and the basket J is remarkably easily used. Particularly, since it is possible to integrate the thin section samples H, in which the same dyeing operation is performed, in the same basket J, high degree of convenience is obtained.

Here, the operation of the above-described thin section preparation device 51 will be described in detail.

First, an immersion process is performed in which the slide glass G is immersed into the immersion position of the storage tank 7. Specifically, the controller 12 operates the driving portion of the slide glass handling mechanism 9 and moves the hand portion 9A to the slide glass storage portion 31. Moreover, after a new slide glass G stored in the slide glass storage portion 31 is held by the hand portion 9A, the controller 12 moves the hand portion 9A to the storage tank 7. Thereafter, the controller 12 moves the hand portion 9A so that the slide glass G is immersed at the state where the other end portion of the slide glass G is inclined at the predetermined angle θ4 with respect to the liquid surface at the immersion position in the storage tank 7. In this case, in the plan view of the XY plane, the slide glass G is immersed so that the first side in the longitudinal direction of the slide glass G is coincident with the X axis direction. Accordingly, the immersion process is completed.

Additionally, simultaneously with the above-described immersion process, a conveyance process is performed in which the thin section M obtained by the main machining operation is conveyed toward the storage tank 7. Specifically, simultaneously with the operation of the stage 4 in the above-described main machining operation, the conveyance belt 53 is run by the slider mechanism 55. In this way, when the conveyance belt 53 is run by the slider mechanism 55, the thin section M which is gradually thinly cut with the draw angle θ2 by the cutting blade 21 is placed on the conveyance belt 53 from the end portion (hereinafter, referred to as a tip portion) of the side positioned at the cutting blade 21 side via the upper portion of the cutting blade 21. That is, since the embedding block B and the cutting blade 21 move relative to each other, the thin section M which is cut by the cutting blade 21 is automatically placed on the conveyance belt 53.

Moreover, when the thin section M is completely separated from the embedding block B, the thin section M is conveyed toward the downstream side (storage tank 7 side) in the running direction T2 in the state where the entire surface of the thin section is placed on the conveyance belt 53.

At this time, as described above, in the present embodiment, the cutting blade 21 is disposed with the draw angle θ2. Accordingly, the thin section M is conveyed along the running direction T2 in the state where the first side of the thin section M is coincident with the X axis direction in the longitudinal direction.

When the thin section M conveyed toward the storage tank 7 reaches a waterline between the conveyance belt 53 and the liquid surface of the storage tank 7, the thin section M is separated from the conveyance belt 53 and is floated on the liquid surface. Specifically, the conveyance belt 53 continuously runs, and thus, the thin section M is sequentially separated from the tip portion, and the separated portion is floated on the liquid surface of the storage tank 7.

In addition, the thin section M is floated on the liquid surface, and thus, the thin section M is spread by the surface tension of the liquid.

Thereafter, when the conveyance belt 53 further is kept running continuously, the tip portion of the thin section M floating on the storage tank 7 reaches the rotary body 61. Then, the thin section M is placed on the rotary body 61 (thin section support body 63) by the rotation of the rotary body 61. In addition, the thin section M is placed on the outer circumferential surface of the thin section support body 63 in the state where the first side in the longitudinal direction is coincident with the X axis direction, and is conveyed along the X axis direction. In this case, the thin section M is supported by the plurality of ring members 64 with intervals in the Y axis direction. Accordingly, the bubbles, which are mixed between the liquid surface and the thin section M when the thin section M is floated on the liquid surface, pass between the ring members 64 and are removed.

Moreover, when the above-described controller 12 detects that the thin section M has reached the rotary body 61, the controller 12 operates the slider mechanism 55 of the thin section conveying mechanism 8. As a result, the Y axis direction component V2$y$ of the conveyance speed vector V2 in the running direction T2 by the conveyance belt 53 is cancelled by the Y axis direction component V1$y$ of the movement speed vector V1 in the direction T1 of the blade edge of the cutting blade 21 by the slider mechanism 55, and thus, the thin section M relatively moves only in the X axis direction with respect to the rotary body 61. Accordingly, in one thin section M, it is possible to decrease the difference of the movement speeds in the Y axis direction between the portion placed on the rotary body 61 and the portion positioned on the conveyance belt 53 and the liquid surface. Accordingly, it is possible to prevent the wrinkling, the rupturing, or the like of the thin section M, and thus, it is possible to smoothly deliver the thin section M to the rotary body 61.

The thin section M, which is conveyed on the rotary body 61, is separated from the rotary body 61 in the waterline between the rotary body 61 and the liquid surface in the downstream side in the conveyance direction T3, and thus, is floated on the liquid again. Specifically, since the rotary body 61 continuously rotates, and thus, the thin section M is sequentially separated from the tip portion, and the separated portion is floated on the liquid surface.

Thereafter, a placement process is performed in which the thin section M conveyed by the rotary body 61 is placed on the slide glass G Specifically, when the above-described controller 12 detects that the tip portion of the thin section M has reached the waterline between the slide glass G and the liquid, the controller 12 operates the driving portion of the slide glass handling mechanism 9, and pulls up the slide glass G. At this time, the controller 12 obliquely pulls up the slide glass G with the predetermined angle θ4. Accordingly, the portion of the thin section M, which has reached the immersion position, is sequentially placed from one end portion to the other end portion in the longitudinal direction of the slide glass G Thereafter, the thin section M is completely placed on the slide glass G, and thus, it is possible to prepare the thin section sample H.

Moreover, the slide glass G to which the thin section M is transferred is conveyed by the slide glass handling mechanism 9, and thus, is stored in the slide glass storage portion 31.

In this way, according to the present embodiment, the thin section M thinly cut with the draw angle θ2 is conveyed along the running direction T2 by the conveyance belt 53 without changing the direction of the thin section M in the state where the first side is coincident with the X axis direction and is spread in the storage tank 7. Thereafter, in the state where the direction of the first side of the thin section M coincident with the X axis direction is maintained, the conveyance direction T3 is converted into the X axis direction by the rotary body 61. Accordingly, in the state where the first side of the thin section M is coincident with the first side of the slide glass G, the thin section M is conveyed to the slide glass handling mechanism 9. As a result, it is possible to place the thin section M in a desired direction with respect to the slide glass G at a desired position on the slide glass G Accordingly, it is possible to prevent the wrinkling, curling, or the like of the thin section M generated when the thin section M is placed on the slide glass G and it is possible to prepare the thin section sample H having high reliability.

In addition, unlike the related art, since it is not necessary to provide the plurality of driving shafts, it is possible to simplify the configuration and decrease the cost.

Moreover, in the present embodiment, the plurality of ring members 64 which are disposed with intervals in the Y axis direction are provided, and the thin section M is supported by the ring members 64 with intervals. Accordingly, it is possible to remove the bubbles which are mixed between the liquid surface and the thin section M when the thin section M is floated on the liquid surface. Therefore, it is possible to prevent the bubbles from being mixed between the slide glass G and the thin section M when the thin section M is placed on the slide glass G, and it is possible to improve adhesion between the slide glass G and the thin section M.

Accordingly, since it is possible to prepare the thin section sample H having higher reliability, it is possible to smoothly perform the post-process (for example, dyeing process, or the like).

Moreover, in the present embodiment, the distance in the X axis direction between the outer circumferential surface of the thin section support body 63 and the upper surface of the conveyance belt 53, and a distance in the X axis direction between the outer circumferential surface of the thin section support body 63 and the slide glass G disposed at the immersion position are set to be equal to or less than the length of the first side of each of the thin sections M, or to be less than the length in the longitudinal direction of each of the thin sections M. Accordingly, a portion of the thin section M always comes into contact with the conveyance belt 53, the thin section support body 63, or the slide glass G That is, since the entirety of the thin section M is not completely floated on the liquid surface, it is possible to deliver the thin section M to the post-process while preventing the change of the posture of the thin section M during the conveyance. Accordingly, it is possible to reliably place the thin section M at a desired position of the slide glass G.

Moreover, the technical scope of the present invention is limited to the above-described embodiment, and various modifications are applied to the above-described embodiment within a scope which does not depart from the gist of the present invention. That is, the configuration or the like of the above-described embodiment is only an example, and the configuration or the like may be appropriately modified.

For example, in the above-described embodiment, the case where the conveyance belt 53 or the slide glass G is set to be inclined to the liquid surface is described. However, the present invention is not limited to this. For example, the conveyance belt 53 or the slide glass G may be disposed to be perpendicular to the liquid surface.

The rotary body 61 may be rotated at all times. In addition, the rotation of the rotary body 61 may be started when it is detected that the tip portion of the thin section M has reached the rotary body 61, and the rotation of the rotary body 61 may be stopped when it is detected that the rear end portion of the thin section M has passed through the rotary body 61.

Moreover, in the above-described embodiment, the case has been described where the thin section support body 63 of the rotary body 61 is configured with slit-shaped intervals in the Y axis direction by the plurality of ring members 64. However, the present invention is not limited to this. The thin section support body 63 of the rotary body 61 may adopt a mesh-shaped thin section support body 63, and may adopt a columnar thin section support body 63.

In addition, in the above-described embodiment, the configuration in which the slider mechanism 55 is provided at the thin section conveying mechanism 8 is described. However, the present invention is not limited to this. The rotary body 61 may move along the direction T1 of the blade edge, and the thin section conveying mechanism 8 and the rotary body 61 may move toward each other in a relative manner.

In addition, in the above-described embodiment, the configuration in which the slider mechanism 55 is operated at the time when the thin section M reaches the rotary body 61 is described. However, the present invention is not limited to this. For example, a configuration in which the slider mechanism slides at the time when the thin section M is separated from the conveyance belt 53 to the liquid surface may be adopted.

In addition, in the above-described embodiment, the configuration in which the conveyance belt 53 runs toward the direction orthogonal to the direction T1 of the blade edge is described. However, the present invention is not limited to this as long as the direction of the first side of the thin section M parallel to the X axis direction is maintained. For example, the conveyance belt 53 may run in a direction intersecting each of the direction T1 of the blade edge of the cutting blade 21 and the X axis direction.

Moreover, in the above-described embodiment, it is described that the side in the longitudinal direction of the slide glass G, the thin section M, or the like is defined as the first side. However, the present invention is not limited to this. For example, the side in the short-length direction of the slide glass G, the thin section M, or the like may be defined as the first side.

Moreover, the shape in the plan view of the embedding block B is not limited to the rectangular shape.

In addition, in the above-described embodiment, the case where the thin section preparation device 51 of the present invention is incorporated into the automatic thin-cutting device 1 is described. However, the present invention is not limited to this. For example, only the thin section preparation device 51 may be used as a single body.

Moreover, in the above-described embodiment, the state where 6 magazines 2 are simultaneously mounted on the carousel 3 is described as an example. However, the present invention is not limited to this. For example, the number of the magazines 2 which are simultaneously mounted on the carousel 3 may be set to an arbitrary number such as one, two, three, four, five, or seven or more.

REFERENCE SIGNS LIST

7 . . . storage tank, 8 . . . thin section conveying mechanism (conveying mechanism), 9 . . . slide glass handling mechanism (substrate disposition mechanism), 21 . . . cutting blade, 51 . . . thin section preparation device, 55 . . . slider mechanism, 61 . . . rotary body, 62 . . . rotary shaft, 64 . . . ring member (support portion), B . . . embedding block, G . . . slide glass (substrate), H . . . thin section sample, M . . . thin section, W . . . liquid

What is claimed is:

1. A thin section preparation device that is capable to cut a thin section from an embedding block in which a biological sample is embedded, and to prepare a thin section sample by placing the thin section on a substrate, the thin section preparation device comprising:
   a cutting blade that is configured to relatively move with respect to the embedding block in an X axis direction in which a first side of the embedding block extends, and to thinly cut the embedding block with a predetermined draw angle in order to cut out the thin section;
   a storage tank that is configured to store a liquid, and to spread the thin section by floating the cut thin section on the liquid;
   a conveying mechanism that is arranged so that a first portion of the conveying mechanism is disposed in a state where the first portion is close to a blade edge of the cutting blade while having a second portion of the conveying mechanism immersed into the liquid, and that is configured to convey the thin section in a direction intersecting in the X axis direction in a plan view of a surface of the embedding block in a state where the first side of the thin section is parallel with the X axis direction;
   a substrate disposition mechanism that is configured to place the thin section floating in the storage tank on the substrate in a state where a first side of the substrate is parallel with the X axis direction in the plan view; and
   a columnar shaped rotary body that is provided between the conveying mechanism and the substrate disposition mechanism, and that is configured to convey the thin section toward the substrate disposition mechanism by rotating in a state where the thin section is placed on an outer circumferential surface of the rotary body,
   wherein the rotary body is configured to be rotatable about a Y axis orthogonal to the X axis direction in the plan view,
   wherein the outer circumferential surface of the rotary body is divided into plurality of support portions configured to support the thin section while having gaps between the plurality of support portions in a plane direction of the thin section so that bubbles between a liquid surface and the thin section can be removed through the gaps, and
   wherein at least a portion of the plurality of the support portions are arranged in a immersed state in the liquid of the storage tank.

2. The thin section preparation device according to claim 1, further comprising:
   a slider mechanism that is configured to move the conveying mechanism and the rotary body relative to each other in a direction of the blade edge of the cutting blade.

3. The thin section preparation device according to claim 1,
   wherein, on the liquid surface of the storage tank, a distance in the X axis direction between the outer circumferential surface of the rotary body and an upper surface of the conveying mechanism, and a distance in the X axis direction between the outer circumferential surface of the rotary body and the substrate disposition mechanism disposed at an immersion position are set to be equal to or less than a length in a longitudinal direction of the thin section, or to be less than the length in the longitudinal direction of the thin section.

\* \* \* \* \*